US008715352B2

(12) United States Patent
Lopez et al.

(10) Patent No.: US 8,715,352 B2
(45) Date of Patent: May 6, 2014

(54) BUCKLING DISC REPLACEMENT

(75) Inventors: Erasmo Lopez, Seattle, WA (US);
SeungKyu Daniel Kwak, Grafton, MA (US); Amie Borgstrom, Stanford, CA (US); John R. Hawkins, Cumberland, RI (US)

(73) Assignee: DePuy Spine, Inc., Raynham, MA (US)

( * ) Notice: Subject to any disclaimer, the term of this patent is extended or adjusted under 35 U.S.C. 154(b) by 953 days.

(21) Appl. No.: 11/610,796

(22) Filed: Dec. 14, 2006

(65) Prior Publication Data

US 2008/0147191 A1    Jun. 19, 2008

(51) Int. Cl.
*A61F 2/44*    (2006.01)
(52) U.S. Cl.
USPC ..................... 623/17.16; 623/17.15
(58) Field of Classification Search
USPC ................. 623/17.11, 17.16, 17.12–17.15
See application file for complete search history.

(56) References Cited

U.S. PATENT DOCUMENTS

| | | | | |
|---|---|---|---|---|
| 3,007,834 A | * | 11/1961 | Moeller et al. | 156/197 |
| 3,867,728 A | * | 2/1975 | Stubstad et al. | 623/17.16 |
| 4,349,921 A | * | 9/1982 | Kuntz | 623/17.16 |
| 4,772,287 A | | 9/1988 | Ray et al. | |
| 4,880,429 A | * | 11/1989 | Stone | 623/14.12 |
| 4,904,260 A | | 2/1990 | Ray et al. | |
| 4,911,718 A | * | 3/1990 | Lee et al. | 623/17.15 |
| 5,171,281 A | * | 12/1992 | Parsons et al. | 623/17.15 |
| 5,562,738 A | | 10/1996 | Boyd et al. | |
| 5,702,450 A | | 12/1997 | Bisserie et al. | |
| 5,716,416 A | | 2/1998 | Lin | |
| 5,928,284 A | | 7/1999 | Mehdizadeh | |
| 6,086,595 A | | 7/2000 | Yonemura et al. | |
| 6,146,419 A | * | 11/2000 | Eaton | 623/11.11 |
| 6,156,040 A | | 12/2000 | Yonemura et al. | |
| 6,179,874 B1 | | 1/2001 | Cauthen | |
| 6,231,609 B1 | | 5/2001 | Mehdizadeh | |
| 6,283,998 B1 | * | 9/2001 | Eaton | 623/17.16 |
| 6,440,168 B1 | | 8/2002 | Cauthen | |
| 6,530,956 B1 | * | 3/2003 | Mansmann | 623/18.11 |
| 6,562,041 B1 | | 5/2003 | Yonemura et al. | |

(Continued)

FOREIGN PATENT DOCUMENTS

| | | |
|---|---|---|
| EP | 1273276 | 1/2003 |
| EP | 1342456 | 9/2003 |

(Continued)

OTHER PUBLICATIONS

International Search Report dated Aug. 1, 2008.

*Primary Examiner* — Michael T Schaper
(74) *Attorney, Agent, or Firm* — Nutter McClennen & Fish LLP

(57) ABSTRACT

An artificial disc replacement implant is provided that includes an implantable body having a superior surface adapted to be positioned adjacent to an endplate of a superior vertebra, and an opposite inferior surface adapted to be positioned adjacent to an endplate of an adjacent inferior vertebrae. The implantable body includes at least one wall formed therein and extending between the superior and inferior surfaces. The wall(s) can be adapted such that, when the implantable body is disposed between the endplates of adjacent superior and inferior vertebrae, the wall(s) will buckle by moving laterally and shorting in height under a load applied thereto by movement of the adjacent vertebrae. The implantable body can also include at least one opening formed adjacent to the wall(s) and extending between the superior and inferior surfaces of the implantable body.

12 Claims, 5 Drawing Sheets

(56) References Cited

U.S. PATENT DOCUMENTS

| | | | |
|---|---|---|---|
| 6,572,653 | B1 | 6/2003 | Simonson |
| 6,610,093 | B1 | 8/2003 | Pisharodi |
| 6,679,915 | B1 | 1/2004 | Cauthen |
| 6,692,495 | B1 | 2/2004 | Zacouto |
| 6,814,737 | B2 | 11/2004 | Cauthen |
| 6,846,328 | B2 | 1/2005 | Cauthen |
| 6,881,228 | B2 | 4/2005 | Zdeblick et al. |
| 6,887,273 | B2 | 5/2005 | Ralph et al. |
| 6,887,274 | B2 | 5/2005 | Ralph et al. |
| 6,893,465 | B2 | 5/2005 | Huang et al. |
| 6,893,466 | B2 | 5/2005 | Trieu |
| 6,896,680 | B2 | 5/2005 | Michelson |
| 6,918,934 | B2 | 7/2005 | Ralph et al. |
| 6,936,070 | B1 | 8/2005 | Muhanna |
| 6,936,071 | B1 | 8/2005 | Marnay et al. |
| 6,958,078 | B2 * | 10/2005 | Goel et al. ............... 623/17.16 |
| 6,960,232 | B2 | 11/2005 | Lyons et al. |
| 6,966,929 | B2 | 11/2005 | Mitchell |
| 6,966,931 | B2 | 11/2005 | Huang et al. |
| 7,004,971 | B2 * | 2/2006 | Serhan et al. ............. 623/17.16 |
| 7,037,340 | B2 | 5/2006 | Gau et al. |
| 7,105,025 | B2 * | 9/2006 | Castro et al. ............. 623/17.16 |
| 7,879,101 | B2 * | 2/2011 | Petit et al. ................ 623/17.15 |
| 8,092,533 | B2 * | 1/2012 | Melkent .................... 623/17.11 |
| 2002/0188300 | A1 | 12/2002 | Arramon et al. |
| 2003/0023312 | A1 * | 1/2003 | Thalgott .................... 623/17.16 |
| 2003/0055427 | A1 | 3/2003 | Graf |
| 2003/0199982 | A1 | 10/2003 | Bryan |
| 2003/0220643 | A1 | 11/2003 | Ferree |
| 2004/0015168 | A1 | 1/2004 | Yonemura et al. |
| 2004/0049280 | A1 | 3/2004 | Cauthen |
| 2004/0127992 | A1 * | 7/2004 | Serhan et al. ............. 623/17.16 |
| 2004/0138749 | A1 | 7/2004 | Zucherman et al. |
| 2004/0138753 | A1 | 7/2004 | Ferree |
| 2004/0143270 | A1 | 7/2004 | Zucherman et al. |
| 2004/0153157 | A1 | 8/2004 | Keller |
| 2004/0153159 | A1 | 8/2004 | Cauthen |
| 2004/0158254 | A1 | 8/2004 | Eisermann |
| 2004/0158328 | A1 | 8/2004 | Eisermann |
| 2004/0167538 | A1 | 8/2004 | Gerber et al. |
| 2004/0181284 | A1 | 9/2004 | Simonson |
| 2004/0181285 | A1 | 9/2004 | Simonson |
| 2004/0186577 | A1 | 9/2004 | Ferree |
| 2004/0225362 | A1 | 11/2004 | Richelsoph |
| 2004/0225363 | A1 | 11/2004 | Richelsoph |
| 2004/0225364 | A1 | 11/2004 | Richelsoph et al. |
| 2004/0225365 | A1 | 11/2004 | Eisermann et al. |
| 2004/0225366 | A1 | 11/2004 | Eisermann et al. |
| 2004/0226098 | A1 * | 11/2004 | Pearce ......................... 5/655.5 |
| 2004/0254644 | A1 | 12/2004 | Taylor |
| 2004/0267369 | A1 | 12/2004 | Lyons et al. |
| 2005/0015150 | A1 | 1/2005 | Lee |
| 2005/0033431 | A1 | 2/2005 | Gordon et al. |
| 2005/0033432 | A1 | 2/2005 | Gordon et al. |
| 2005/0033435 | A1 | 2/2005 | Belliard et al. |
| 2005/0033437 | A1 | 2/2005 | Bao et al. |
| 2005/0033439 | A1 | 2/2005 | Gordon et al. |
| 2005/0038445 | A1 | 2/2005 | Errico et al. |
| 2005/0038515 | A1 | 2/2005 | Kunzler |
| 2005/0038516 | A1 | 2/2005 | Spoonamore |
| 2005/0043740 | A1 | 2/2005 | Haid et al. |
| 2005/0043800 | A1 | 2/2005 | Paul et al. |
| 2005/0043801 | A1 | 2/2005 | Trieu et al. |
| 2005/0043802 | A1 | 2/2005 | Eisermann et al. |
| 2005/0043803 | A1 | 2/2005 | Schultz et al. |
| 2005/0049590 | A1 | 3/2005 | Alleyne et al. |
| 2005/0049623 | A1 | 3/2005 | Moore et al. |
| 2005/0049707 | A1 | 3/2005 | Ferree |
| 2005/0060035 | A1 | 3/2005 | Errico et al. |
| 2005/0065610 | A1 | 3/2005 | Pisharodi |
| 2005/0065611 | A1 | 3/2005 | Huppert et al. |
| 2005/0085909 | A1 | 4/2005 | Eisermann |
| 2005/0085916 | A1 | 4/2005 | Li et al. |
| 2005/0085917 | A1 | 4/2005 | Marnay et al. |
| 2005/0096746 | A1 | 5/2005 | Bryan et al. |
| 2005/0102027 | A1 | 5/2005 | Ferree |
| 2005/0102029 | A1 | 5/2005 | Blain |
| 2005/0102030 | A1 | 5/2005 | Yuksel et al. |
| 2005/0107881 | A1 | 5/2005 | Alleyne et al. |
| 2005/0113925 | A1 | 5/2005 | Carli |
| 2005/0113926 | A1 | 5/2005 | Zucherman et al. |
| 2005/0113928 | A1 | 5/2005 | Cragg et al. |
| 2005/0113929 | A1 | 5/2005 | Cragg et al. |
| 2005/0119747 | A1 * | 6/2005 | Fabris Monterumici et al. .................... 623/17.11 |
| 2005/0119749 | A1 | 6/2005 | Lange |
| 2005/0119750 | A1 | 6/2005 | Studer |
| 2005/0119752 | A1 | 6/2005 | Williams et al. |
| 2005/0124992 | A1 | 6/2005 | Ferree |
| 2005/0125061 | A1 | 6/2005 | Zucherman et al. |
| 2005/0125062 | A1 | 6/2005 | Biedermann et al. |
| 2005/0125063 | A1 | 6/2005 | Matge et al. |
| 2005/0125064 | A1 | 6/2005 | Ralph et al. |
| 2005/0125065 | A1 | 6/2005 | Zucherman et al. |
| 2005/0130929 | A1 | 6/2005 | Boyd |
| 2005/0131536 | A1 | 6/2005 | Eisermann et al. |
| 2005/0131540 | A1 | 6/2005 | Trieu |
| 2005/0131541 | A1 * | 6/2005 | Trieu ........................ 623/17.11 |
| 2005/0131542 | A1 | 6/2005 | Benzel et al. |
| 2005/0131543 | A1 | 6/2005 | Benzel et al. |
| 2005/0131544 | A1 | 6/2005 | Kuras et al. |
| 2005/0143820 | A1 | 6/2005 | Zucherman et al. |
| 2005/0143821 | A1 | 6/2005 | Zdeblick et al. |
| 2005/0143824 | A1 | 6/2005 | Richelsoph et al. |
| 2005/0149188 | A1 | 7/2005 | Cook et al. |
| 2005/0149196 | A1 | 7/2005 | Zucherman et al. |
| 2005/0154461 | A1 | 7/2005 | Humphreys et al. |
| 2005/0154464 | A1 | 7/2005 | Humphreys et al. |
| 2005/0154465 | A1 | 7/2005 | Hodges et al. |
| 2005/0154466 | A1 | 7/2005 | Humphreys et al. |
| 2005/0154467 | A1 | 7/2005 | Peterman et al. |
| 2005/0154468 | A1 | 7/2005 | Rivin |
| 2005/0159818 | A1 | 7/2005 | Blain |
| 2005/0165407 | A1 | 7/2005 | Diaz |
| 2005/0165484 | A1 | 7/2005 | Ferree |
| 2005/0165485 | A1 | 7/2005 | Trieu |
| 2005/0165486 | A1 | 7/2005 | Trieu |
| 2005/0171550 | A1 | 8/2005 | Marik |
| 2005/0171608 | A1 | 8/2005 | Peterman et al. |
| 2005/0171609 | A1 | 8/2005 | Humphreys et al. |
| 2005/0171610 | A1 | 8/2005 | Humphreys et al. |
| 2005/0171611 | A1 | 8/2005 | Stoy et al. |
| 2005/0177239 | A1 | 8/2005 | Steinberg |
| 2005/0187631 | A1 | 8/2005 | Van Hoeck et al. |
| 2005/0187632 | A1 | 8/2005 | Zubok et al. |
| 2005/0187633 | A1 | 8/2005 | Ferree |
| 2005/0192670 | A1 | 9/2005 | Zubok et al. |
| 2005/0192671 | A1 | 9/2005 | Bao et al. |
| 2005/0192674 | A1 | 9/2005 | Ferree |
| 2005/0197702 | A1 * | 9/2005 | Coppes et al. ............. 623/17.12 |
| 2005/0197705 | A1 | 9/2005 | Arnin et al. |
| 2005/0197706 | A1 | 9/2005 | Hovorka et al. |
| 2005/0203626 | A1 | 9/2005 | Sears et al. |
| 2005/0203627 | A1 | 9/2005 | Choksey et al. |
| 2005/0209696 | A1 | 9/2005 | Lin et al. |
| 2005/0216084 | A1 | 9/2005 | Fleischmann et al. |
| 2005/0216086 | A1 | 9/2005 | Marik et al. |
| 2005/0216092 | A1 | 9/2005 | Marik et al. |
| 2005/0222683 | A1 | 10/2005 | Berry |
| 2005/0228497 | A1 | 10/2005 | Ferree et al. |
| 2005/0228500 | A1 | 10/2005 | Kim et al. |
| 2005/0234553 | A1 | 10/2005 | Gordon |
| 2005/0234554 | A1 | 10/2005 | Ralph et al. |
| 2005/0234556 | A1 | 10/2005 | Kretschmer |
| 2005/0240273 | A1 | 10/2005 | Khandkar et al. |
| 2005/0246022 | A1 | 11/2005 | Zubok et al. |
| 2005/0246024 | A1 | 11/2005 | Zeegers |
| 2005/0251260 | A1 * | 11/2005 | Gerber et al. ............. 623/17.13 |
| 2005/0251261 | A1 | 11/2005 | Peterman |
| 2005/0251262 | A1 | 11/2005 | De Villiers et al. |
| 2005/0256576 | A1 | 11/2005 | Moskowitz et al. |
| 2005/0256577 | A1 | 11/2005 | Baumgartner et al. |
| 2005/0256580 | A1 | 11/2005 | Marissen |
| 2005/0256581 | A1 | 11/2005 | Songer et al. |

(56) References Cited

U.S. PATENT DOCUMENTS

| | | | |
|---|---|---|---|
| 2005/0261772 A1 | 11/2005 | Filippi et al. | |
| 2005/0261773 A1 | 11/2005 | Ferree | |
| 2005/0267580 A1 | 12/2005 | Suddaby | |
| 2005/0267581 A1 | 12/2005 | Marnay et al. | |
| 2005/0267582 A1 | 12/2005 | Ferree et al. | |
| 2006/0047341 A1* | 3/2006 | Trieu | 623/17.12 |
| 2006/0247781 A1* | 11/2006 | Francis | 623/17.16 |
| 2006/0259146 A1* | 11/2006 | Navarro et al. | 623/17.14 |
| 2007/0233245 A1* | 10/2007 | Trieu | 623/17.11 |
| 2008/0140199 A1* | 6/2008 | Briest | 623/17.11 |

FOREIGN PATENT DOCUMENTS

| | | |
|---|---|---|
| EP | 1527759 | 5/2005 |
| EP | 1532948 | 5/2005 |
| EP | 1532950 | 5/2005 |
| EP | 1555964 | 7/2005 |
| EP | 1572036 | 9/2005 |
| EP | 1572037 | 9/2005 |
| JP | 2004329937 | 11/2004 |
| JP | 2005137905 | 6/2005 |
| WO | WO-9909896 | 3/1999 |
| WO | WO-03071992 | 9/2003 |
| WO | WO-2004002291 | 1/2004 |
| WO | WO-2004016205 | 2/2004 |
| WO | WO-2004016217 | 2/2004 |
| WO | WO-2004019828 | 3/2004 |
| WO | WO-2004019830 | 3/2004 |
| WO | WO-2004026186 | 4/2004 |
| WO | WO-2004026187 | 4/2004 |
| WO | WO-2004028415 | 4/2004 |
| WO | WO-2004033516 | 4/2004 |
| WO | WO-2004041075 | 5/2004 |
| WO | WO-2004041131 | 5/2004 |
| WO | WO 2004039291 | 5/2004 |
| WO | WO-2004047691 | 6/2004 |
| WO | WO-2004049980 | 6/2004 |
| WO | WO-2004052234 | 6/2004 |
| WO | WO-2004054477 | 7/2004 |
| WO | WO-2004054478 | 7/2004 |
| WO | WO-2004054479 | 7/2004 |
| WO | WO-2004054480 | 7/2004 |
| WO | WO-2004058098 | 7/2004 |
| WO | WO-2004064692 | 8/2004 |
| WO | WO-2004071344 | 8/2004 |
| WO | WO-2004071347 | 8/2004 |
| WO | WO-2004073561 | 9/2004 |
| WO | WO-2004080355 | 9/2004 |
| WO | WO-2004098465 | 11/2004 |
| WO | WO-2004098466 | 11/2004 |
| WO | WO-2005011522 | 2/2005 |
| WO | WO-2005013862 | 2/2005 |
| WO | WO-2005033437 | 4/2005 |
| WO | WO-2005037028 | 4/2005 |
| WO | WO-2005037148 | 4/2005 |
| WO | WO-2005039455 | 5/2005 |
| WO | WO-2005041793 | 5/2005 |
| WO | WO-2005041818 | 5/2005 |
| WO | WO-2005046534 | 5/2005 |
| WO | WO-2005051228 | 6/2005 |
| WO | WO-2005051243 | 6/2005 |
| WO | WO-2005051246 | 6/2005 |
| WO | WO-2005053579 | 6/2005 |
| WO | WO-2005053580 | 6/2005 |
| WO | WO-2005058194 | 6/2005 |
| WO | WO-2005063150 | 7/2005 |
| WO | WO-2005067824 | 7/2005 |
| WO | WO-2005070278 | 8/2005 |
| WO | WO-2005070349 | 8/2005 |
| WO | WO-2005070350 | 8/2005 |
| WO | WO-2005070351 | 8/2005 |
| WO | WO-2005070352 | 8/2005 |
| WO | WO-2005070353 | 8/2005 |
| WO | WO-2005070354 | 8/2005 |
| WO | WO-2005072660 | 8/2005 |
| WO | WO-2005074839 | 8/2005 |
| WO | WO-2005084590 | 9/2005 |
| WO | WO-2005089680 | 9/2005 |
| WO | WO-2005092247 | 10/2005 |
| WO | WO-2005092250 | 10/2005 |
| WO | WO-2005094732 | 10/2005 |
| WO | WO-2005094733 | 10/2005 |
| WO | WO-2005094734 | 10/2005 |
| WO | WO-2005094736 | 10/2005 |
| WO | WO-2005094737 | 10/2005 |
| WO | WO-2005097006 | 10/2005 |
| WO | WO-2005104996 | 11/2005 |
| WO | WO-2005107654 | 11/2005 |
| WO | WO-2005107656 | 11/2005 |

* cited by examiner

BUCKLING DISC REPLACEMENT

FIELD OF THE INVENTION

The present invention relates to methods and devices for replacing a spinal disc.

BACKGROUND OF THE INVENTION

Disease, advancing age, and trauma can lead to changes in various bones, discs, joints, and ligaments of the body. Some changes and trauma often manifest themselves in the form of damage or degeneration to a spinal disc. This condition often results in chronic back pain, which can be anywhere from mild to severe. This pain can sometimes be eliminated by spinal fusion in which two adjacent vertebral bodies are jointed together after removing the intervening intervertebral disc. A prosthetic device is usually placed between the two adjacent vertebral bodies, in place of the removed disc, to fill the space left by the removed disc and to allow bone to grow between the two vertebral bodies.

More recently, spinal disc replacement implants have been developed that allow motion between the adjacent vertebrae, thereby restoring normal function to the vertebrae. These implants generally rely on spherical, cylindrical, or otherwise shaped bearing surfaces to allow movement between two components. While many of the current designs are successful, some of the challenges with current designs include wear levels, fatigue under loading, range of motion, and surgical window size required to implant the disc replacement.

Accordingly, there remains a need for improved methods and devices for replacing a spinal disc.

SUMMARY OF THE INVENTION

The present invention generally provides methods and devices for replacing a spinal disc. In one embodiment, an artificial disc replacement implant is provided and includes an implantable body having a superior surface adapted to be positioned adjacent to an endplate of a superior vertebra, and an opposite inferior surface adapted to be positioned adjacent to an endplate of an adjacent inferior vertebra. The implantable body includes at least one wall formed therein and extending between the superior and inferior surfaces. The wall(s) can be adapted such that, when the implantable body is disposed between the endplates of adjacent superior and inferior vertebrae, the wall(s) will buckle by moving laterally and shorting in height under a load applied thereto by movement of the adjacent vertebrae. The implantable body can also include at least one opening formed adjacent to the wall(s) and extending between the superior and inferior surfaces of the implantable body.

The implantable body can also have a variety of shapes. In one embodiment the implantable body can have a semi-circular shape with a plurality of walls spaced radially around the implantable body. In another embodiment, the body can be substantially C-shaped with opposed first and second terminal ends, and a first pair of walls positioned adjacent the first terminal end and a second pair of walls positioned adjacent the second terminal end. In yet another embodiment, the body can have a circular shape with a plurality of walls spaced radially around the implantable body and extending from a substantial midpoint of the implantable body to an outer sidewall of the implantable body. In an exemplary embodiment, at least one of the walls has a geometry that differs from a geometry of at least another one of the walls such that at least one of the walls has a buckling strength that is less than a buckling strength of another one of the walls.

In yet another embodiment, an artificial disc replacement implant is provided and includes an implantable body that is adapted to be disposed between adjacent vertebrae of a spine and that is adapted to maintain the adjacent vertebrae at a distance apart from one another. The implantable body can have at least one opening formed therein such that predetermined portions of the implantable body are adapted to buckle in response to movement of adjacent vertebrae when implanted therebetween. The implantable body can be formed from a variety of materials but in an exemplary embodiment the implantable body is formed from an elastomeric material.

The implant can include any number of opening having various configurations. In one embodiment, the opening can extend between superior and inferior surfaces of the implantable body. In another embodiment, the implant can include a first opening positioned adjacent to a first terminal end wall of the implantable body, and a second opening positioned adjacent to a second opposite terminal end wall of the implantable body. The first and second terminal end walls of the implantable body can be adapted to buckle in response to movement of adjacent vertebrae when implanted therebetween. The implant can also include a third opening extending through the implantable body adjacent to the first opening such that the implantable body includes a first inner wall extending between the first and third openings, and a fourth opening extending through the implantable body adjacent to the second opening such that the implantable body includes a second inner wall extending between the second and fourth openings. The first and second inner walls can be adapted to buckle in response to movement of adjacent vertebrae when implanted therebetween. In yet another embodiment, the first and second terminal end walls of the implantable body can have a buckling strength that is less than a buckling strength of the first and second inner walls such that the first and second terminal end walls will buckle before the first and second inner walls buckle in response to movement of adjacent vertebrae when implanted therebetween. In other aspects, the implant can include a plurality of axially-extending openings defining a plurality of axially-extending posts. At least one of the posts can have a geometry that differs from a geometry of at least another one of the posts such that at least one of the posts has a buckling strength that is less than a buckling strength of another one of the posts.

Exemplary methods for controlling movement between adjacent vertebrae of a spine are also provided. In one embodiment, the method can include positioning an elastomeric implant between adjacent vertebrae such that at least one wall extending through the implant extends between opposed endplates of the adjacent vertebrae and the at least one wall buckles in response to movement of adjacent vertebrae to thereby control movement between the adjacent vertebrae. In an exemplary embodiment, the wall(s) is positioned to buckle in response to at least one of flexion, extension, and lateral bending of the adjacent vertebrae. The implant can have a variety of configurations. For example, the elastomeric implant can include a first half positioned on a first lateral side of a disc space formed between the adjacent vertebrae, and a separate second half positioned on a second opposite lateral side of the disc space. In another embodiment, the elastomeric implant can be positioned between first and second endplate members that are positioned adjacent to the opposed endplates of the adjacent vertebrae. The method can also include, prior to positioning the elastomeric implant, introducing the implant using one or a posterior surgical approach, a postereo-lateral surgical approach, an anterior surgical approach, and an antereo-lateral surgical approach.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1A:
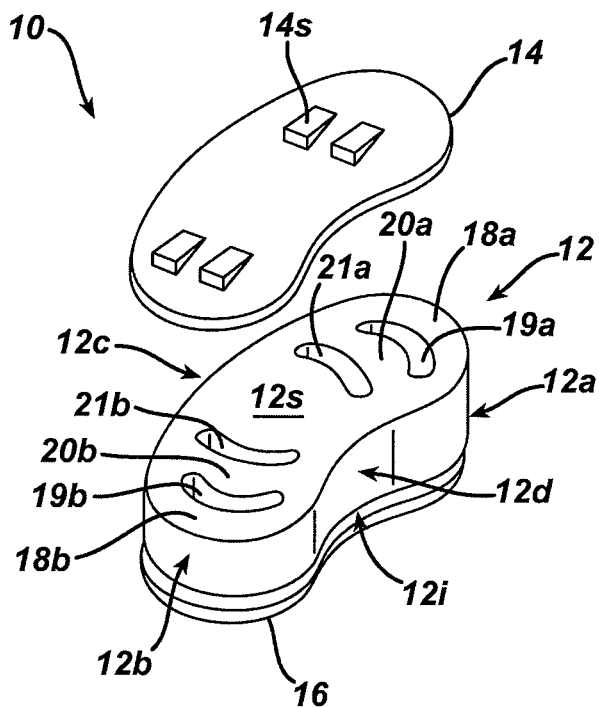
FIG. 1A is a perspective view of one embodiment of an artificial disc replacement implant having first and second pairs of walls formed in opposed ends thereof and adapted to buckle in response to movement of adjacent vertebrae.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides devices and methods for replacing a spinal disc, and in particular devices and methods that rely on buckling to control movement of adjacent vertebrae. Buckling refers to the displacement mode characterized by a sudden large displacement of a structural member that is subjected to compressive stresses where the actual compressive stresses at failure are greater than the ultimate compressive stresses, i.e., the buckling strength, that the structure is capable of withstanding. In an exemplary embodiment, an artificial disc replacement implant is provided and it includes at least one structural member that is adapted to buckle in response to movement of the adjacent vertebrae. When the implant is disposed between adjacent vertebrae, the structural member(s) will provide resistance to movement of the adjacent vertebrae. When the forces applied to the structural member(s) are greater than the buckling strength of the structural member(s), the structural member(s) will buckle and collapse. In the collapsed configuration, the resistance to movement applied to the adjacent vertebrae by the implant is significantly decreased. The structural member(s) can, however, easily "bounce back" or return to the unbuckled configuration to once again provide a desired amount of resistance to movement.

In an exemplary embodiment, an implant can be specifically configured to have desired buckling properties based on the intended use. For example, an implant can be configured to have structural members or walls, also referred to herein as columns, positioned at predetermined locations that will buckle when a predetermined load is applied thereto to thereby control particular types of movement between two adjacent vertebrae. The buckling strength or maximum axial load of a particular structural member or column can be calculated using the Euler formula, which is:

$$F = (K\pi^2 EI)/l^2$$

where F is the maximum or critical force, E is the modulus of elasticity, I is the area moment of inertia, l is the unsupported length of the column, and K is a constant whose value depends upon the conditions of the end support of the columns. Where both ends of the column are free, K is 1; where both ends of the column are fixed, K is 4; where one end of the column is fixed and the other end is free, K is 2; and where one end of the column is fixed and the other end is free to move laterally, K is ¼. While the buckling strength of a structural member configured to control movement between adjacent vertebrae can vary, by way of non-limiting example an implant can be configured having one or more structural members that have a buckling strength that corresponds to about 1 newton meter of moment induced on a spinal segment. This desired buckling strength can be used to determine the necessary configuration of each column in the implant.

A person skilled in the art will appreciate that the particular configuration, location, and quantity of structural members can vary to control particular types of movement, such as flexion, extension, and lateral bending. The buckling strength of each structural member can also be adapted to provide a desired amount of resistance to movement of the adjacent vertebrae. In an exemplary embodiment, the implant includes at least one wall that is adapted to buckle when a force is applied thereto that is greater than a buckling strength of the wall. The wall can be defined by the shape and configuration of the implant body. For example, the body can include one or more holes or openings formed therein that define a wall adjacent to the opening. The location of each wall can also correspond to the desired movement to be controlled. For example, the implant can include posterior and anterior walls that are positioned in posterior and anterior regions of a disc space to control flexion and extension. The implant can also or alternatively include lateral walls that are positioned in lateral regions of a disc space to control lateral bending. The structural member(s) can also have fixed ends to increase the buckling strength, or they can have free ends to reduce the buckling strength. In addition to modifying the geometry of the implant to control particular types of movement between the adjacent vertebrae, the materials used to form the implant can also function to cause the structural member(s) of the implant to buckle. For example, various portions of the implant can be formed from materials have properties, such as elasticity and/or stiffness, that differ from the properties of other portions of the implant. A person skilled in the art will appreciate that a variety of techniques can be used to provide an implant having one or more structural members that buckle to control movement between adjacent vertebrae.

By way of non-limiting example, FIGS. 1A-7 illustrate various exemplary embodiments of implants having one or more structural members that are adapted to buckle to control movement between adjacent vertebrae. As noted above, a person skilled in the art will appreciate that the particular configuration of the implant, as well as the configuration of each structural member, can vary depending on the desired movement to be controlled and the desired buckling properties.

Figure 1B:
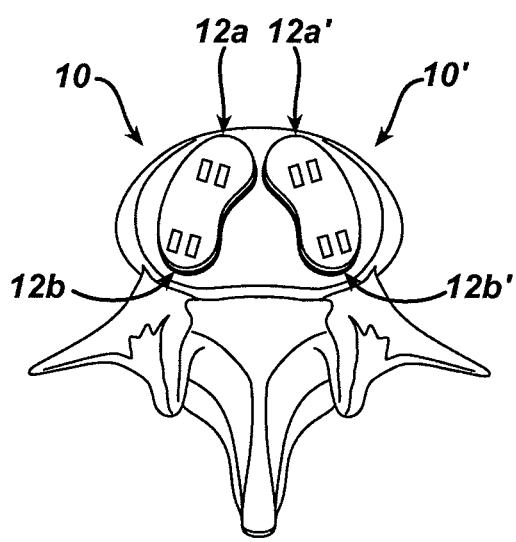
FIG. 1B is a top view of two of the implants of FIG. 1A positioned on a vertebral body.

FIGS. 1A-1B illustrate one embodiment of an implant 10 that is adapted to be positioned between opposed endplates of adjacent vertebral bodies. The illustrated implant 10 has a generally elongate body 12 with opposed superior and inferior surfaces 12s, 12i that are adapted to be positioned between superior and inferior endplates of adjacent vertebrae. The shape of the body 12 can vary, but in the illustrated embodiment the body 12 has a shape that is configured to occupy a lateral portion of a disc space, rather than occupying the entire disc space. In particular, the elongate body 12 has a slightly curved or C-shaped configuration such that the body 12 includes opposed anterior and posterior ends 12a, 12b and opposed first and second lateral sides 12c, 12d extending between the anterior and posterior ends 12a, 12b. The particular dimensions of the implant 10 can also vary, but preferably the implant 10 has a height measured between the superior and inferior surfaces 12s, 12i that allows the implant 10 to function as a load-bearing element during movement of the adjacent vertebrae. In other words, the height is preferably sufficient to span across the disc space and contact the opposed endplates of the adjacent vertebrae.

As further shown in FIG. 1A, the implant 10 can also optionally include first and second endplate members 14, 16 adapted to mate to or be positioned adjacent to the superior and inferior surfaces 12s, 12i of the body 12. Each endplate member 14, 16 can have various shapes and sizes, but in an exemplary embodiment each endplate member 14, 16 can have a shape that corresponds to a shape of the body 12. Each endplate member 14, 16 can also optionally include features to engage bone, such as one or more surface features, such as teeth 14s, formed thereon. In use, the body 12 can be merely positioned between the endplate members 14, 16, or it can be mated to the endplate members 14, 16 using various techniques known in the art, such as adhesives or other mechanical or chemical mating techniques. When implanted, the endplate members 14, 16 can be positioned adjacent to the superior and inferior endplates of adjacent vertebrae to help prevent movement or expulsion of the implant 10 from the disc space.

The body 12 can also include one or more structural members adapted to buckle when a predetermined load is applied thereto. In the illustrated embodiment, the anterior and posterior ends 12a, 12b of the body 12 each include a pair of walls 18a, 20a, 18b, 20b, respectively, that extend between the superior and inferior surfaces 12s, 12i. In particular, each end 12a, 12b includes an outer wall 18a, 18b and an adjacent inner wall 20a, 20b. The walls 18a, 20a, 18b, 20b are formed or defined by bores or openings extending through the body 12 between the superior and inferior surfaces 12s, 12i. As shown, the anterior end 12a of the body 12 has a first opening 19a formed between the outer wall 18a and the inner wall 20a, and a second opening 21a formed adjacent to the inner wall 20a on a side opposite the first opening 19a. Thus, the inner wall 20a is defined by the first and second openings 19a, 21a. The posterior end 12b of the body 12 likewise has a first opening 19b formed between the outer wall 18b and the inner wall 20b, and a second opening 21b formed adjacent to the inner wall 20b on a side opposite the first opening 19b. Thus, the inner wall 20b is defined by the first and second openings 19b, 21b. The shape of the openings 19a, 21a, 19b, 21b can define the shape of each wall 18a, 20a, 18b, 20b. As shown in FIG. 1A, each opening 19a, 21a, 19b, 21b is in the form of an elongate, partially curved or C-shaped slot extending between the opposed sides 12c, 12d of the body 12, i.e., in a direction substantially parallel to the anterior and posterior ends 12a, 12b. The openings 19a, 21a, 19b, 21b also extend through the body 12 between the superior and inferior surfaces 12s, 12i. Thus, each wall 18a, 20a, 28b, 20b has a generally elongate, partially curved or C-shaped configuration. In an exemplary embodiment, the walls 18a, 20a, 18b, 20b are curved in the direction of motion, as will be discussed in more detail below. The particular radius of the curvature can vary to obtain the desired buckling strength, but in an exemplary embodiment the walls 18a, 20a, 18b, 20b have only a slight curvature so as to increase the buckling strength of each wall. The size of each wall 18a, 20a, 18b, 20b can also vary to obtain the desired buckling strength. For example, walls 18a, 20a, 18b, 20b with a small width or thickness will decrease the buckling strength, while walls 18a, 20a, 18b, 20b with a greater width or thickness will increase the buckling strength of the wall.

FIG. 1B illustrates the implant 10 of FIG. 1A in use. As shown, two implants 10, 10' having a configuration as described above with respect to FIG. 1A can be positioned between adjacent vertebrae. One of the implants 10 can be positioned on a first lateral side of a disc space, and the other implant 10' can be positioned on an opposed lateral side of the disc space. The implants 10, 10' can be oriented such that the anterior end 12a, 12a', of each implant 10, 10' is positioned adjacent to an anterior side of the disc space, and the opposed posterior end 12b, 12b' is positioned adjacent to a posterior side of the disc space. As a result, the walls (not shown) located on the anterior end 12a, 12a' of each implant 10, 10' will be positioned in the anterior side of the disc space, and the walls (not shown) located on the posterior end 12b, 12b' of the implant 10, 10' will be positioned in the posterior side of the disc space. During flexion of the adjacent vertebrae, i.e., increasing the distance between the posterior side of each vertebra, the walls located on the anterior side of the disc space will be compressed and thus will provide resistance to flexion. When the force applied to the walls by the vertebrae is greater than the buckling strength of the walls, the walls will buckle, i.e., collapse. Similarly, during extension of the adjacent vertebrae, i.e., increasing the distance between the anterior side of each vertebra, the walls located on the posterior side of the disc space will be compressed and thus will provide resistance to extension. When the force applied to the walls by the vertebrae is greater than the buckling strength of the walls, the walls will buckle, i.e., collapse. Thus, the implants 10, 10' provide posterior and anterior buckling to accommodate flexion and extension of adjacent vertebrae.

The portion located between the second openings (not shown) in each implant 10, 10' can also be effective to provide resistance to vertical loading, as this portion will generally be positioned along the vertical axis of the spine.

Due to the positioning of the walls relative to the vertebrae, the outer walls 18a, 18b (FIG. 1A) will likely buckle prior to the inner walls 20a, 20b. The walls can, however, be configured to have differing buckling strengths to achieve a desired result. This can be achieved by altering the geometry of each wall. Preferably, however, the walls are curved in the direction of movement. In this embodiment, where the implant 10 is configured to control flexion and extension, movement will occur at the anterior and posterior ends 12a, 12b of the implant 10. Thus, the walls can be curved outward toward the adjacent anterior and posterior ends 12a, 12b. Preferably, the curvature is very slight so as to still provide a sufficient buckling strength, as a greater curvature would reduce the buckling strength. The buckling strength can also be optimized by altering the material properties of the walls, for example by increasing or decreasing the thickness of each wall, or forming each wall from a different material, etc.

Figure 2A:
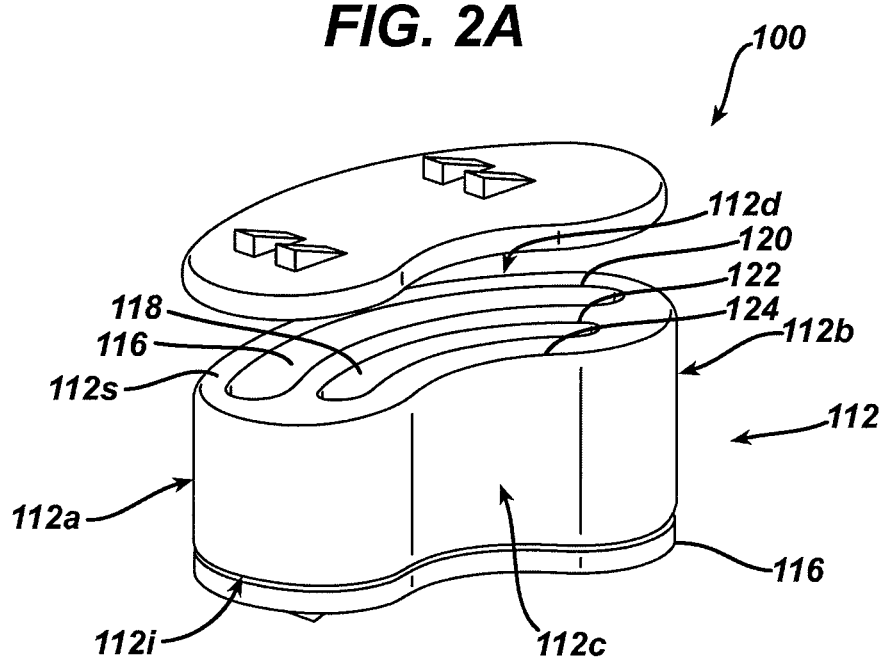
FIG. 2A is a perspective view of another embodiment of an artificial disc replacement implant having three walls extending between opposed ends thereof and adapted to buckle in response to movement of adjacent vertebrae.
Figure 2B:
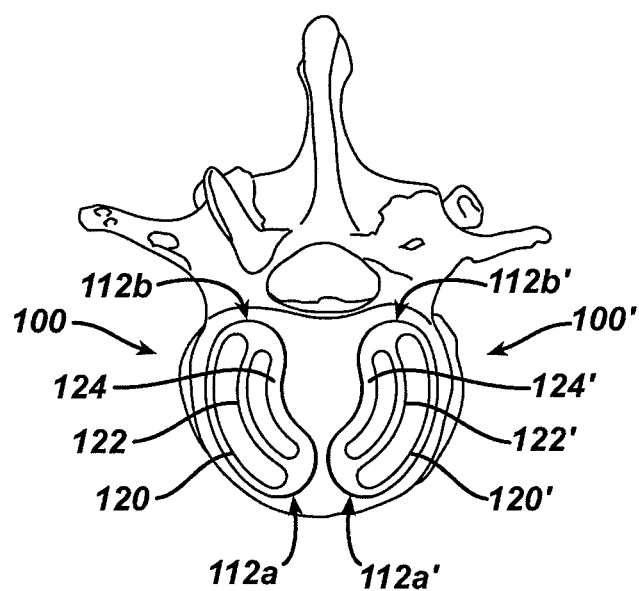
FIG. 2B is a top view of two of the implants of FIG. 2A positioned on a vertebral body.

FIGS. 2A-2B illustrate another embodiment of an implant 100 that is adapted to be positioned between opposed endplates of adjacent vertebral bodies, and that relies on buckling to control various movements between the adjacent vertebrae. The implant 100 is similar to implant 10 described above, and generally includes an elongate, slightly curved or C-shaped body 112 having superior and inferior surfaces 112s, 112i, anterior and posterior ends 112a, 112b, and opposed sides 112c, 112d. The implant 100 also includes opposed endplate members 114, 116 that are positioned adjacent to the superior and inferior surfaces 112s, 112i, and that are adapted to engage the endplates of adjacent vertebrae when the implant 100 is implanted. While implant 100 is similar to implant 10, in this embodiment the structural members are configured to provide lateral buckling to accommodate lateral bending. In particular, the body 112 includes first and second laterally-extending openings 116, 118 formed therein and extending between the anterior and posterior ends 112a, 112b thereof. The openings 116, 118 define first, second, and third laterally-extending walls 120, 122, 124. The second wall 112 is positioned between the first and third wall 120, 124, and thus extends along a mid-portion of the implant 100. As with the previous embodiment, each wall 120, 122, 124 can have a slightly curved configuration. The walls can, however, have a straight configuration or have any other shape to achieve the desired buckling effect.

FIG. 2B illustrates the implant 100 in use. As shown, two implants 100, 100' having a configuration as described above with respect to FIG. 2A can be positioned between adjacent vertebrae. One of the implants 100 can be positioned on a first lateral side of a disc space, and the other implant 100' can be positioned on an opposed lateral side of the disc space. The implants 100, 100' can be oriented such that the anterior end 112a, 112a', of each implant 100, 100' is positioned adjacent to an anterior side of the disc space, and the opposed posterior end 112b, 112b' is positioned adjacent to a posterior side of the disc space. As a result, the walls 120, 122, 124, 120', 122', 124' will be positioned adjacent to the lateral sides of the disc space and will extend in a posterior-anterior direction. During lateral bending of the adjacent vertebrae, i.e., increasing/decreasing the distance between the lateral side of each vertebra, the walls will be compressed and thus will provide resistance to lateral bending. For example, if the patient bends to the right, the implant 100 positioned in the right lateral side of the disc space will provide resistance as the distance between the right lateral side of each vertebra decreases. When the force applied to the walls by the vertebrae is greater than the buckling strength of the walls, the walls will buckle, i.e., collapse. Wall 120 will likely buckle before wall 122, and wall 122 will likely buckle before wall 124 due to the positioning of the walls and the amount of force applied thereto during lateral bending. Walls 122 and 124 may also not buckle depending on the amount of lateral bending, and the particular properties of the implant 100.

Figure 3A:
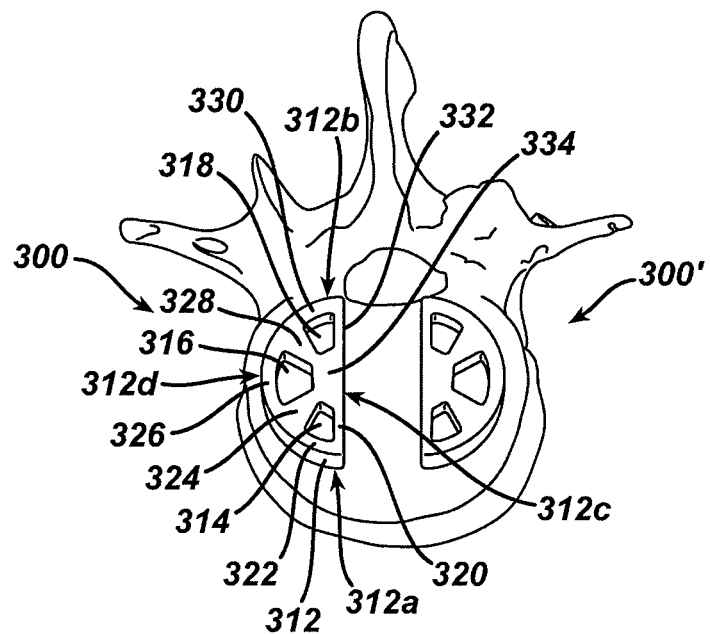
FIG. 3A is a perspective view of yet another embodiment of an artificial disc replacement implant having a semi-circular configuration with openings formed radially therein and defining walls that are adapted to buckle in response to movement of adjacent vertebrae.
Figure 3B:
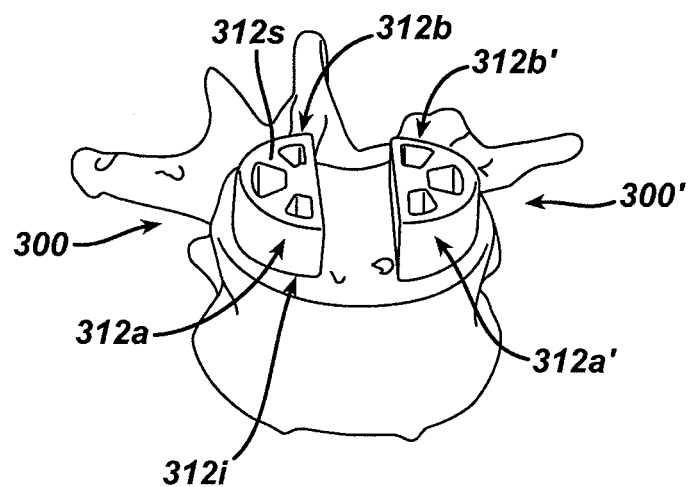
FIG. 3B is a perspective view of two of the implants of FIG. 3A positioned on a vertebral body.

FIGS. 3A and 3B illustrate yet another embodiment of an implant 300 that is adapted to be positioned between opposed endplates of adjacent vertebral bodies, and that relies on buckling to control various movements between the adjacent vertebrae. While two implants 300, 300' are shown, each implant can have the same or similar configuration and thus only one implant will be described. As shown, the implant 300 generally includes a semi-circular shaped body 312 having superior and inferior surfaces 312s, 312i (FIG. 3B), anterior and posterior ends 312a, 312b, and a substantially planar side 312c and an opposed curved side 312d. While not shown, the implant 300 can also optionally include opposed endplate members that are positioned adjacent to the superior and inferior surfaces 312s, 312i, and that are adapted to engage the endplates of adjacent vertebrae when the implant 300 is implanted.

As further shown in FIGS. 3A and 3B, the body 312 can include one or more structural members that are configured to provide lateral buckling and posterior-anterior buckling. In particular, the body 312 can include several openings formed therein and spaced radially around the body 312. In the illustrated embodiment, the body 312 includes a first opening 314 positioned adjacent to the anterior end 312a of the body 312, a second opening 316 positioned the curved side 312d of the body, and a third opening 318 positioned adjacent to the posterior end 312b of the body 312. While the shape of each opening 314, 316, 318 can vary, in an exemplary embodiment the openings 314, 316, 318 have a somewhat triangular or trapezoidal configuration. As a result of the openings 314, 316, 318, the body 312 includes multiple structural members that can buckle when a force is applied thereto that is greater than a buckling strength of the member. In particular, the first opening 314 can be surrounded by three walls 320, 322, 324 that could potentially buckle. A portion of the planar side 312c adjacent to the first opening 314 can form the first wall 320, a portion of the curved side 312d adjacent to the first opening 314 can form the second wall 322, and a third wall 324 can be formed between the first and second openings 314, 316. A portion of the curved side 312d adjacent to the second opening 316 can form a fourth wall 326, and a fifth wall 328 can be formed between the second and third openings 316, 318. A portion of the curved side 312d adjacent to the third opening 318 can form a sixth wall 330, and a portion of the planar side 312c adjacent to the third opening 318 can form an eighth wall 332.

In use, as shown, two implants 300, 300' having a similar configuration can be positioned between adjacent vertebrae. One of the implants 300 can be positioned on a first lateral side of a disc space, and the other implant 300' can be positioned on an opposed lateral side of the disc space. The implants 300, 300' can be oriented such that the anterior end 312a, 312a', of each implant 300, 300' is positioned adjacent to an anterior side of the disc space, and the opposed posterior end 312b, 312b' is positioned adjacent to a posterior side of the disc space. Referring to implant 300, walls 320 and 332 will extend in a posterior-anterior direction, while walls 322, 326, and 330 will extend adjacent to the lateral edge of the disc space. The walls 324, 328 located between the openings 314, 316, 318 will extend in a generally lateral direction.

During lateral bending, flexion, and extension of the adjacent vertebrae certain walls may buckle while others do not depending on the particular location of the wall as well as the particular configuration of each wall. For example, during lateral bending, one or more of the walls 322, 326, 330 located on the curved side 312*d* of the body 312 may buckle when a force is applied thereto that is greater than the buckling strength of the wall. Upon further lateral bending, walls 324 and 328 can also buckle if a sufficient force is applied thereto. During flexion and extension, walls 330 and 322 can buckle, as well as walls 320 and 332. As with previous embodiment, the core or central portion 334 of the body 312 can provide resistance to vertical loading.

FIGS. 4A-4D illustrate yet another embodiment of an implant having buckling structures for controlling movement between adjacent vertebrae. In this embodiment, the implant 400 has a generally cylindrical shape with an outer wall 402 extending around a perimeter thereof, and several radial walls 406*a-g* extending between a central core 404 and the outer wall 402. The central core 404 can provide resistance to vertical loading, while the outer wall 402 and the radial walls 406*a-g* can provide resistance to lateral bending, flexion, and extension of the adjacent vertebrae.

Figure 4A:
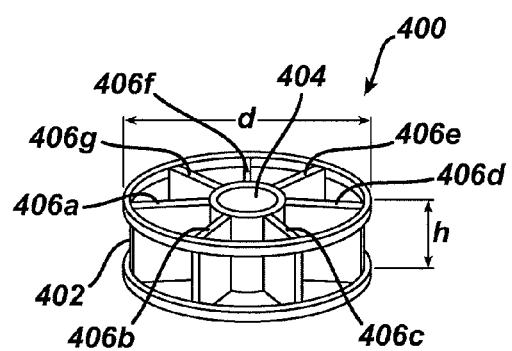
FIG. 4A is a perspective view of another embodiment of an artificial disc replacement implant having a circular configuration with radially-extending walls formed therein and adapted to buckle in response to movement of adjacent vertebrae.
Figure 4B:
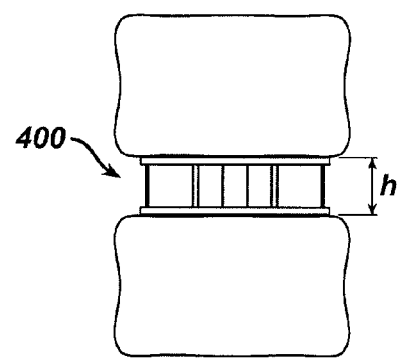
FIG. 4B is a side view of the implant of FIG. 4A disposed between adjacent vertebrae.
Figure 4C:
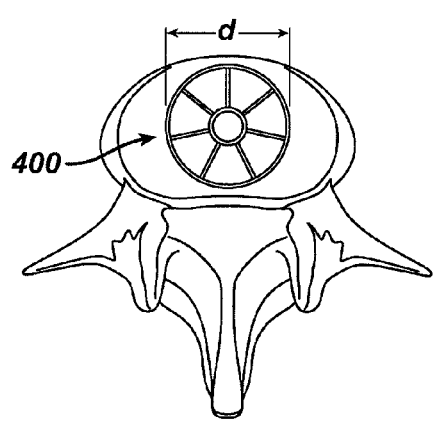
FIG. 4C is a top view of the implant of FIG. 4A positioned on a vertebral body.
Figure 4D:
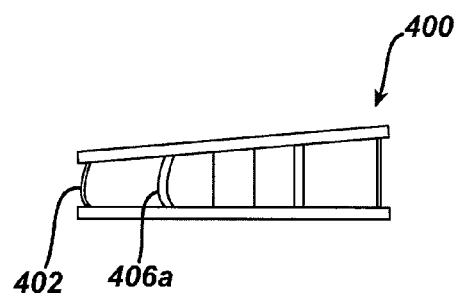
FIG. 4D is a cross-sectional view of the implant of FIG. 4A, showing a portion of the implant in a buckled position.
Figure 5:
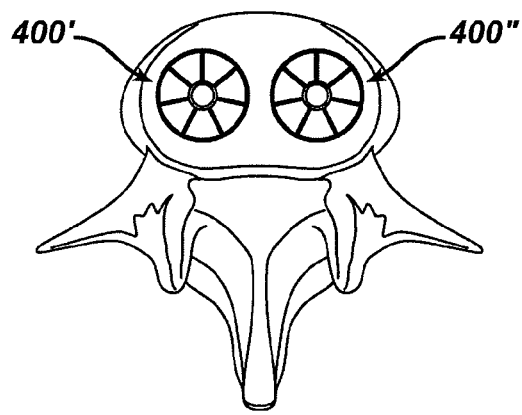
FIG. 5 is a top view of two of the implants of FIG. 4A positioned on a vertebral body.

FIGS. 4B and 4C illustrate the implant 400 in use, and as shown the implant 400 can have a shape and size that matches the shape and size of the endplate of a vertebra. In particular, the implant 400 can have a diameter d that is adapted to span across the disc space, and a height h that is adapted to span between the endplates of the adjacent vertebrae. The central core 404 will thus be aligned with a longitudinal axis of the spine to provide resistance to vertical loading, and the radial walls 406*a-g* will extend radially from the central core 404 to provide buckling resistance to lateral bending, flexion, and extension. Various portions of the outer wall 402 can also buckle when a force is applied thereto by the adjacent vertebrae that is greater than the buckling strength of the outer wall 402. FIG. 4D illustrates a cross-section of the implant 400 in a buckled state. As shown, a portion of the outer wall 402, as well as one of the radial walls, e.g., wall 406*a*, has collapsed or buckled in response to a force applied thereto. Once the applied force decreases so as to be less than the buckling strength, the walls 402, 406*a* will spring back to the unbuckled configuration, shown in FIGS. 4A-4C.

While implant 400 is shown having a size and shape configured to match the size and shape of an endplate of a vertebrae, the implant 400 can have size and shape that allows the implant 400 to occupy only one lateral side of a disc space. This is illustrated, for example, in FIG. 5 which shows two implants 400', 400" positioned on opposed lateral sides of a disc space. Each implant 400', 400" will thus provide buckling resistance to various movements between the adjacent vertebrae.

Figure 6:
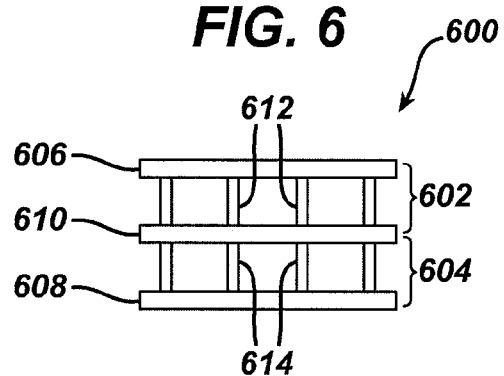
FIG. 6 is a side view of yet another embodiment of an artificial disc replacement implant having superior and inferior walls adapted to buckle in response to movement of adjacent vertebrae.

FIG. 6 illustrates yet another embodiment of an implant 600 that is adapted to be positioned between opposed endplates of adjacent vertebral bodies, and that relies on buckling to control various movements between the adjacent vertebrae. In this embodiment, the implant 600 includes superior and inferior portions 602, 604, each having various structural members that are adapted to buckle when a predetermined force is applied thereto. In particular, the superior portion 602 includes a superior endplate member 606 adapted to be positioned adjacent to an endplate of a superior vertebrae, and the inferior portion 604 includes an inferior endplate member 608 adapted to be positioned adjacent to an endplate of an inferior vertebra. A middle plate member 610 is disposed between the superior and inferior portions 602, 604. Each plate member 606, 608, 610 can have various configurations, and they can be solid or have a circular shape with one or more openings formed therein. The plate members 606, 608, 610 can also be substantially rigid or they can be flexible. As further shown, the superior portion 602 can include several structural members or walls 612 that extend between endplate member 606 and plate member 610, and the inferior portion 604 can include several structural members or walls 614 that extend between endplate member 608 and plate member 610. As with the previous embodiments, the walls 612, 614 can be configured to buckle when a force is applied thereto that is greater than a buckling strength of the wall. The particular location of each wall within the disc space, as well as the particular buckling strength of each wall, will determine which wall buckles in response to certain movements between the adjacent vertebrae.

Figure 7:
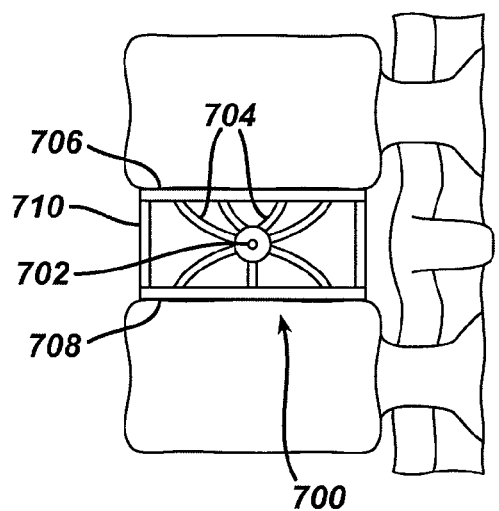
FIG. 7 is a side view of yet another embodiment of an artificial disc replacement implant having a wall that extend radially outward from a center portion of the implant, showing the implant positioned between adjacent vertebrae.

FIG. 7 illustrates yet another embodiment of an implant 700 that is adapted to be positioned between opposed endplates of adjacent vertebral bodies, and that relies on buckling to control various movements between the adjacent vertebrae. In this embodiment, the implant 700 has a central core 702 which several structural members or inner walls 704 that extend radially outward from the central core 702 in various directions. Each inner wall 704 has a generally curved configuration and extends outward and toward a superior or inferior endplate member 706, 708. The implant 700 can also include an outer wall 710 extending around a perimeter thereof and extending between the superior and inferior endplate members 706, 708. In use, the inner walls 704 can provide resistance to vertical load placed on the implant 700, and the outer wall 702 can be configured to buckle in response to movement between the adjacent vertebrae. Depending on the range of movement, the inner walls 704 could also be configured to buckle.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. An artificial disc replacement implant, comprising:
    an implantable body having a superior surface, and an opposite inferior surface, the implantable body including at least one wall formed therein and extending between the superior and inferior surfaces, the at least one wall being formed by c-shaped openings extending through the superior and inferior surfaces, each opening being continuously enclosed, and being adapted such that, when the implantable body is disposed between endplates of adjacent superior and inferior vertebrae, an inner surface and an outer surface of the at least one wall will buckle in a same direction under a load applied thereto by movement of the adjacent vertebrae;
    a superior endplate coupled to the superior surface of the implantable body, the superior endplate having at least one anchoring member formed thereon and configured to engage the endplate of the superior vertebra; and
    an inferior endplate coupled to the inferior surface of the implantable body, the inferior endplate having at least one anchoring member formed thereon and configured to engage the endplate of the inferior vertebra.

2. The implant of claim 1, wherein the implantable body is formed from an elastomeric material.

3. The implant of claim 1, wherein the implantable body is substantially C-shaped with opposed first and second terminal ends, and wherein the at least one wall comprises a first pair of walls positioned adjacent the first terminal end and a second pair of walls positioned adjacent the second terminal end.

4. The implant of claim 1, wherein the at least one wall comprises a plurality of walls, and wherein at least one of the walls has a geometry that differs from a geometry of at least another one of the walls such that the at least one of the walls has a buckling strength that is less than a buckling strength of the at least another one of the walls.

5. An artificial disc replacement implant, comprising:
an implantable body having two opposite sidewalls extending between opposed superior and inferior surfaces, the implantable body being adapted to be disposed between adjacent vertebrae of a spine and to maintain the adjacent vertebrae at a distance apart from one another, and the implantable body having a first C-shaped elongate opening that is elongated towards the opposite sidewalls, and a second C-shaped elongate opening that is elongated towards the opposite sidewalls, the first C-shaped opening and the second C-shaped opening being curved in opposite directions, and the first and second C-shaped openings being continuously enclosed, and the first and second C-shaped openings extending through the superior and inferior surfaces such that predetermined portions of the implantable body are adapted to buckle in response to movement of the adjacent vertebrae when implanted therebetween;
further comprising a first endplate member disposed on the superior surface of the implantable body and a second endplate member disposed on the inferior surface of the implantable body;
wherein the first endplate member has at least one anchoring member formed thereon and configured to engage an endplate of a superior vertebra and the second endplate member has at least one anchoring member formed thereon and configured to engage an endplate of an inferior vertebra.

6. The implant of claim 5, wherein the implantable body is formed from an elastomeric material.

7. The implant of claim 5, wherein the first C-shaped opening is positioned adjacent to a first terminal end wall of the implantable body, and the second C-shaped opening is positioned adjacent to a second opposite terminal end wall of the implantable body, the first and second terminal ends walls of the implantable body being adapted to buckle in response to movement of the adjacent vertebrae when implanted therebetween.

8. The implant of claim 7, further comprising a third C-shaped opening extending through the implantable body adjacent to the first C-shaped opening such that the implantable body includes a first inner wall extending between the first and third C-shaped openings, and a fourth C-shaped opening extending through the implantable body adjacent to the second C-shaped opening such that the implantable body includes a second inner wall extending between the second and fourth C-shaped openings, the first and second inner walls being adapted to buckle in response to movement of the adjacent vertebrae when implanted therebetween.

9. The implant of claim 8, wherein the first and second terminal end walls of the implantable body have a buckling strength that is less than a buckling strength of the first and second inner walls such that the first and second terminal end walls will buckle before the first and second inner walls buckle in response to movement of the adjacent vertebrae when implanted therebetween.

10. The implant of claim 5, wherein the implantable body is substantially C-shaped with opposed first and second terminal ends, and further includes a third C-shaped opening positioned adjacent the first terminal end and a fourth C-shaped opening positioned adjacent the second terminal end.

11. The implant of claim 10, wherein the first and third C-shaped openings define a first plurality of walls and the second and fourth C-shaped openings define a second plurality of walls.

12. The implant of claim 11, wherein at least one of the first plurality of walls has a geometry that differs from a geometry of at least another one of the first plurality of walls such that the at least one of the first plurality of walls has a buckling strength that is less than a buckling strength of the at least another one of the first plurality of walls and at least one of the second plurality of walls has a geometry that differs from a geometry of at least another one of the second plurality of walls such that the at least one of the second plurality of walls has a buckling strength that is less than a buckling strength of the at least another one of the second plurality of walls.

* * * * *